United States Patent [19]

Ohnishi et al.

[11] 4,390,694

[45] Jun. 28, 1983

[54] METHOD FOR PREPARING STABLE CRYSTALS OF SALT OF CEFTIZOXIME

[75] Inventors: Norio Ohnishi, Kyoto; Rinta Ibuki, Ashiya, both of Japan

[73] Assignee: Fujisawa Pharmaceutical Co., Ltd., Osaka, Japan

[21] Appl. No.: 283,805

[22] Filed: Jul. 16, 1981

[30] Foreign Application Priority Data

Jul. 22, 1980 [JP] Japan ................... 55-100680

[51] Int. Cl.³ .................... A61K 31/545; C07D 501/04
[52] U.S. Cl. ....................... 544/22; 424/246; 544/16
[58] Field of Search ................ 544/16, 22, 26, 27; 424/246

[56] References Cited

U.S. PATENT DOCUMENTS

4,294,960  10/1981  Takaya et al. ................ 544/22

*Primary Examiner*—Nicholas S. Rizzo
*Attorney, Agent, or Firm*—Oblon, Fisher, Spivak, McClelland & Maier

[57] ABSTRACT

A method for preparing stable crystals of a salt of Ceftizoxime which comprises mixing an aqueous solution of a salt of Ceftizoxime and isopropyl alcohol and collecting the precipitating crystals. Crystals obtained in this manner are more stable than the crystals obtained from prior art methods involving mixed solvents of water and ethanol.

8 Claims, No Drawings

METHOD FOR PREPARING STABLE CRYSTALS OF SALT OF CEFTIZOXIME

This invention relates to a method for preparing stable crystals of a salt of ceftizoxime and to a method for preparing a pharmaceutical preparation containing the stable crystals.

One of the objects of this invention is to provide a method for preparing stable crystals of a salt of ceftizoxime in good yield, and another object of this invention is to provide a method for preparing a pharmaceutical preparation containing said stable crystals.

"Ceftizoxime" is a kind of cephalosporin compound posessing strong antimicrobial activity and has a following chemical formula:

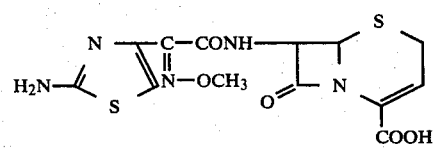

which is referred to as "CZX" hereinafter in this specification.

It has been known that sodium salt of CZX can be obtained by crystallization from aqueous ethanol [Offenlegungsschrift No. 2810922]. According to this known method, the product tends to be contaminated by a kind of unstable crystals of sodium salt of CZX. In order to prevent such a contamination, the content of ethanol in the mixed solvent for crystallization must be less than about 90%. The product obtained by the crystallization from such a solvent is not contaminated by the unstable crystals, but the using of such a solvent results low yield of the product.

The inventors of this invention have studied for preparing stable crystals of a salt of CZX free from the contamination by the unstable crystals in sufficient yield, and found that the crystallization from a mixed solvent of water and isopropyl alcohol gives unexpectedly the stable crystals only in high yield.

The method of this invention for preparing the stable crystals of a salt of CZX is conducted by mixing an aqueous solution of a salt of CZX and isopropyl alcohol and collecting the precipitating crystals.

The salt of CZX may be the one more soluble in water than free CZX, and preferably an alkali metal salt such as sodium salt or potassium salt.

The concentration of a salt of CZX in the aqueous solution to be mixed is not critical, and preferably 30 to 50 w/v % for obtaining the product efficiently.

The ratio of the aqueous solution and isopropyl alcohol to be mixed is not critical, and preferably 1:2–4 and more preferably 1:3 in volume. The mixing of these components may be conducted by adding isopropyl alcohol to the aqueous solution, or conversely adding the aqueous solution to isopropyl alcohol. In case it is desired to obtain the crystals having particle size of 30 to 50μ, the aqueous solution is added to isopropyl alcohol with stirring.

The stirring of the mixture and collection of the precipitating crystals can be conducted at ambient temperature by conventional manner.

Thus obtained di-hydrate of a salt of CZX is more stable than the crystals obtained from the aforementioned mixed solvent of water and ethanol.

The crystals of dihydrate of a salt of CZX obtained above can be dehydrated to give anhydrous crystals by dryness. The dryness can be conducted by conventional manner, and preferably carried out under reduced pressure at ambient temperature or under warming. Thus obtained anhydrous crystals of a salt of CZX are as stable as the crystals of dihydrate of a salt of CZX and can be rapidly dissolved in water. When the crystals of dihydrate of salt of CZX are washed with isopropyl alcohol in advance to the dryness, the anhydrous crystals of better quality can be obtained.

An injection preparation containing the above-mentioned crystals of dihydrate of a salt of CZX or anhydrous crystals of a salt of CZX can be preferably prepared as follows.

The aqueous solution of a salt of CZX and isopropyl alcohol to be mixed are subjected to sterilized filtration in advance to the mixing respectively, and the subsequent mixing of the aqueous solution and isopropyl alcohol, collection of the precipitating crystals by filtration and optional washing of said crystals with sterilized isopropyl alcohol are carried out in sterilized and closed circumstances. Thus obtained crystals are suspended in sterilized isopropyl alcohol in the same circumstances, and the suspension is filled in each vial and dried under reduced pressure in each vial under sterilized condition. The vials containing the stable crystals are finally sealed under the same sterilized condition.

Thus prepared injection preparation contains the stable crystals, namely the crystals of dihydrate of a salt of CZX or anhydrous crystals of a salt of CZX only, and accordingly the effect of a salt of CZX as a medicine can be fully exhibited even after a long term of storage.

And further, the injection preparation prepared by the above-mentioned method is free from the contamination by particular matter and accordingly can be used safely.

The following Example is given only for illustrating the method of this invention.

EXAMPLE

Ceftizoxime (100 g) was added to a solution of sodium hydroxide (10.5 g) in distilled water to give an aqueous solution of sodium salt of ceftizoxime. The aqueous solution was subjected to sterilized filtration and the filtrate was added to sterilized isopropyl alcohol in a sterilized and closed vessel with stirring at ambient temperature. The precipitating crystals of dihydrate of sodium salt of ceftizoxime were collected by filtration in the closed vessel, and washed with sterilized isopropyl alcohol (150 ml) three times. Thus obtained crystals were suspended in sterilized isopropyl alcohol (100 ml), and the suspension was poured into each vial of 10 ml volume. The suspension in each vial was dried in vacuo at ambient temperature for 10 hrs. and then in vacuo at 50° C. for 3 hrs. to give anhydrous crystals of sodium salt of ceftizoxime Thereafter, each vial was sealed under sterilized condition to give the injection preparation, the contents of which are dissolved in distilled water just before using.

The activity of anhydrous crystals of sodium salt of ceftizoxime thus obtained was not drop even after storing at 50° C. for 3 months, and any change of the appearance of the contents was not observed. The contents in each vial was completely dissolved in distilled water (3 ml) in 15 seconds.

We claim:

1. A method for preparing stable crystals of an alkali metal salt of ceftizoxime, which comprises adding an aqueous solution of the salt of ceftizomime to isopropyl alcohol, and collecting the precipitating crystals.

2. The method of claim 1, wherein the salt of ceftizoxime is sodium salt of ceftizoxime.

3. The method of claim 2, according to which the crystals of di-hydrate of sodium salt of ceftizoxime are prepared.

4. The method of claim 2, wherein the collected crystals are dried to give anhydrous crystals of sodium salt of ceftizoxime.

5. The method of claim 1, wherein the collected crystals are washed with isopropyl alcohol, suspended in isopropyl alcohol and dried.

6. The method of claim 5, wherein the aqueous solution and isopropyl alcohol to be mixed are subjected to sterilized filtration in advance to the mixing and isopropyl alcohol for washing and suspending is also subjected to sterilized filtration before use, respectively.

7. The method of claim 6, wherein the mixing of the aqueous solution of a salt of ceftizoxime and isopropyl alcohol, collection of the precipitating crystals, washing and suspending of the crystals are carried out in sterilized and closed circumstances.

8. The method of claim 7, wherein the suspension of a salt of ceftizoxime is filled in each vial and dried under sterilized condition, and the vials are sealed under the same sterilized condition.

* * * * *